US008050759B2

(12) United States Patent
Stegemann et al.

(10) Patent No.: US 8,050,759 B2
(45) Date of Patent: Nov. 1, 2011

(54) SUBCUTANEOUS ICD WITH SEPARATE CARDIAC RHYTHM SENSOR

(75) Inventors: Berthold Stegemann, Aachan (DE); Hans-Juergen Bruns, Eggermühlen (DE)

(73) Assignee: Medtronic, Inc., Minneapolis, MN (US)

( * ) Notice: Subject to any disclaimer, the term of this patent is extended or adjusted under 35 U.S.C. 154(b) by 584 days.

(21) Appl. No.: 11/343,677

(22) Filed: Jan. 31, 2006

(65) Prior Publication Data

US 2007/0179540 A1 Aug. 2, 2007

(51) Int. Cl.
*A61N 1/39* (2006.01)
(52) U.S. Cl. ......................................................... 607/17
(58) Field of Classification Search .................... 607/17, 607/129–131
See application file for complete search history.

(56) References Cited

U.S. PATENT DOCUMENTS

| 4,987,897 A * | 1/1991 | Funke .............................. 607/32 |
| 5,113,859 A | 5/1992 | Funke |
| 5,331,966 A | 7/1994 | Bennett et al. |
| 6,141,588 A * | 10/2000 | Cox et al. ............................ 607/9 |
| 6,751,502 B2 * | 6/2004 | Daum et al. ......................... 607/8 |
| 6,788,970 B1 * | 9/2004 | Park et al. .......................... 607/17 |
| 7,200,437 B1 * | 4/2007 | Nabutovsky et al. .............. 607/9 |
| 2002/0035380 A1 * | 3/2002 | Rissmann et al. .................. 607/4 |
| 2004/0220626 A1 | 11/2004 | Wagner |
| 2004/0220629 A1 | 11/2004 | Kamath et al. |
| 2004/0230280 A1 | 11/2004 | Cates et al. |
| 2005/0197674 A1 * | 9/2005 | McCabe et al. .................... 607/9 |
| 2005/0245971 A1 | 11/2005 | Brockway et al. |

FOREIGN PATENT DOCUMENTS

WO W09826840 A 6/1998

OTHER PUBLICATIONS

International Search Report, PCT/US2007/060944, Jan. 6, 2007, 7 Pages.

* cited by examiner

*Primary Examiner* — Scott Getzow
*Assistant Examiner* — Amanda Patton
(74) *Attorney, Agent, or Firm* — Michael C. Soldner

(57) ABSTRACT

A cardiac rhythm sensor positioned on or close to the heart senses electrical or mechanical activity and transmits a cardiac rhythm signal wirelessly to a subcutaneous ICD. Arrhythmia detection and delivery of therapy are performed by the SubQ ICD based upon the cardiac rhythm signal received from the sensor.

20 Claims, 3 Drawing Sheets

SUBCUTANEOUS ICD WITH SEPARATE CARDIAC RHYTHM SENSOR

BACKGROUND OF THE INVENTION

The present invention relates to implantable medical devices. In particular, the invention relates to a subcutaneous implantable cardioverter defibrillator (SubQ ICD) which receives a rhythm signal wirelessly from an implantable cardiac rhythm sensor positioned on or close to the epicardium.

Implantable cardioverter defibrillators are used to deliver high energy cardioversion or defibrillation shocks to a patient's heart when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by the ICD.

Currently, ICD's use endocardial or epicardial leads which extend from the ICD housing through the venous system to the heart. Electrodes positioned in or adjacent to the heart by the leads are used for pacing and sensing functions. Cardioversion and defibrillation shocks are generally applied between a coil electrode carried by one of the leads and the ICD housing, which acts as an active can electrode.

A SubQ ICD differs from the more commonly used ICD's in that the housing is typically smaller and is implanted subcutaneously. The SubQ ICD does not require leads to be placed in the bloodstream. Instead, the SubQ ICD makes use of one or more electrodes on the housing, together with a subcutaneous lead that carries a defibrillation coil electrode and a sensing electrode.

The absence of endocardial or epicardial electrodes make rhythm and arrhythmia sensing more challenging with the SubQ ICD. Sensing of atrial activation is limited since the atria represent a small muscle mass, and the atrial signals are not sufficiently detectable thoracically. Muscle movement, respiration, and other physiological signal sources and environmental noises also can affect the ability to sense ECG signals and detect arrhythmias with a SubQ ICD.

BRIEF SUMMARY OF THE INVENTION

An implantable cardioverter defibrillator system includes a SubQ ICD and a separate cardiac rhythm sensor that is positioned on or close to the heart. The cardiac rhythm sensor senses electrical or mechanical activity of the heart and transmits a signal wirelessly to the SubQ ICD. The SubQ ICD uses the signal from the cardiac rhythm sensor for arrhythmia detection and delivery of therapy.

DETAILED DESCRIPTION

Figure 1:
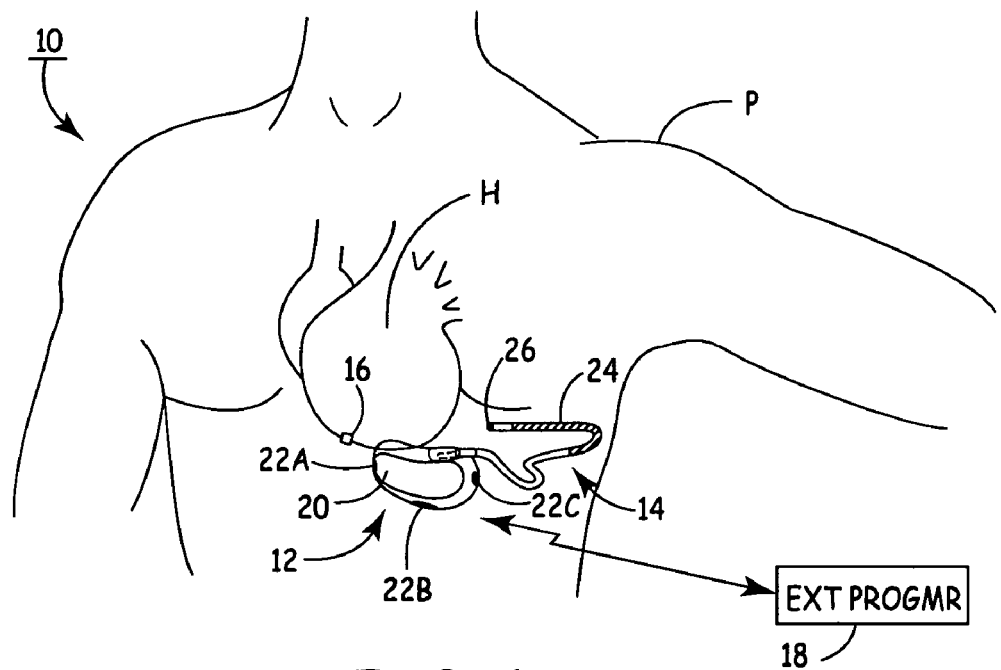
FIG. 1 depicts a SubQ ICD and a separate cardiac rhythm sensor implanted in a patient.

FIG. 1 shows implantable cardioverter defibrillator (ICD) system 10, which includes SubQ ICD 12, subcutaneous sensing and cardioversion/defibrillation therapy delivery lead 14, cardiac rhythm sensor 16, and external programmer 18.

Housing or canister 20 of SubQ ICD 12 is subcutaneously implanted outside the ribcage of patient P, anterior to the cardiac notch, and carries three subcutaneous electrodes 22A-22C. Lead 14 extends from housing 20 and is tunneled subcutaneously laterally and posteriorly to the patient's back at a location adjacent to a portion of a latissimus dorsi mucle. Electrode coil 24 and sensing electrode 26 are located at the distal end of lead 14. Heart H is disposed between the SubQ ICD housing 20 and distal electrode coil 24 of lead 14.

SubQ ICD 12 contains signal processing and therapy delivery circuitry to detect bradycardia and tachycardia conditions and to apply appropriate pacing and defibrillation shocking pulses to heart H. The pacing pulses are applied using electrodes 22A-22C. The shocking pulses are applied between coil electrode 24 and electrically conductive housing or can electrode 20 of SubQ ICD 12. Communication between SubQ ICD 12 and external programmer 18 is provided by an RF communication link.

Sensing of cardiac activity is performed by cardiac rhythm sensor 16, which is a small device separate from SubQ ICD 12 and which is positioned on or close to the epicardium of heart H using a minimally invasive approach. Sensor 16, which carries its own power source, is capable of sensing either electrical or mechanical activity of heart H, and then transmitting a cardiac rhythm signal representing the sensed activity to SubQ ICD 12 and lead 14. The transmitted cardiac rhythm signal from sensor 16 is received by SubQ ICD 12 using electrodes 22A-22C, or by lead 14 together with one of electrodes 22A-22C. SubQ ICD 12 uses the received cardiac rhythm signal to analyze cardiac activity and make therapy decisions.

Figure 2B:
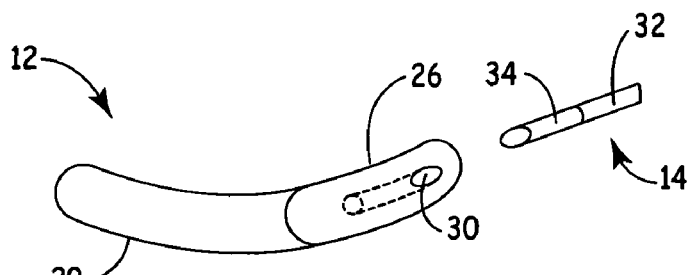
FIGS. 2A and 2B are front and top views of the SubQ ICD and associated subcutaneous lead.
Figure 2A:
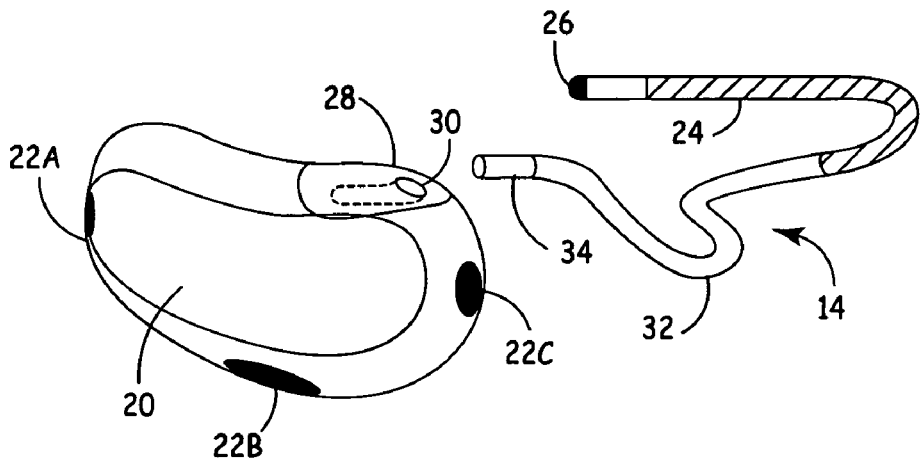

FIGS. 2A and 2B are front and top views of SubQ ICD 12. Housing 20 is an ovoid with a substantially kidney-shaped profile. The ovoid shape of housing 20 promotes ease of subcutaneous implant and minimizes patient discomfort during normal body movement and flexing of the thoracic musculature. Housing 20 contains the electronic circuitry of SubQ ICD 12. Header 28 and connector 30 provide an electrical connection between distal electrode coil 24 and distal sensing electrode 26 on lead 14 and the circuitry within housing 20.

Subcutaneous lead 14 includes distal defibrillation coil electrode 24, distal sensing electrode 26, insulated flexible lead body 32 and proximal connector pin 34. Distal sensing electrode 26 is sized appropriately to match the sensing impedance of electrodes 22A-22C.

Electrodes 22A-22C are welded into place on the flattened periphery of canister 20 and are connected to electronic circuitry inside canister 20. Electrodes 22A-22C may be constructed of flat plates, or alternatively, spiral electrodes (as described in U.S. Pat. No. 6,512,940) and mounted in a non-conductive surround shroud (as described in U.S. Pat. Nos. 6,522,915 and 6,622,046). Electrodes 22A-22C shown in FIG. 2 are positioned on housing 20 to form orthogonal signal vectors.

Figure 3:
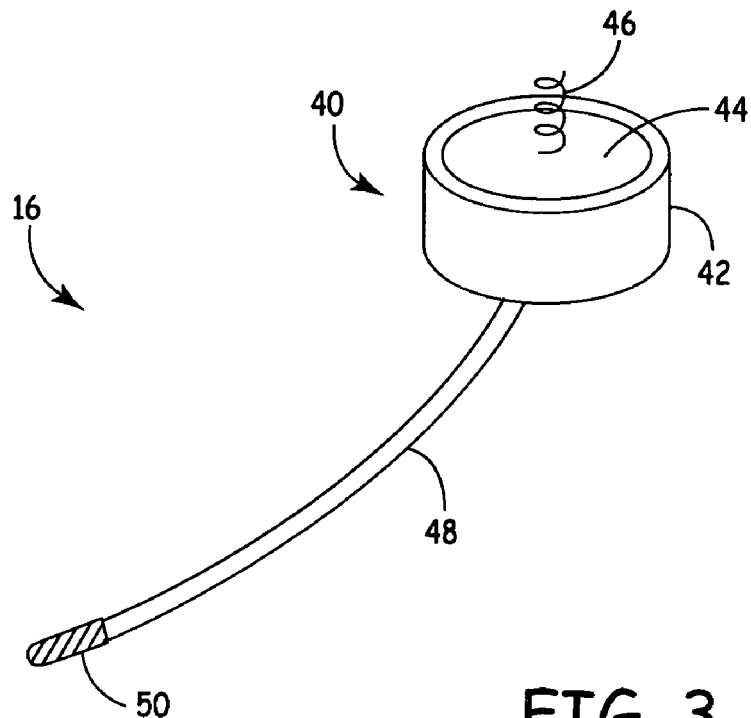
FIG. 3 is a perspective view of one embodiment of the cardiac rhythm sensor.

FIG. 3 shows an embodiment of cardiac rhythm sensor 16 which includes housing 40, ring electrode 42, tip electrode 44, fixation screw 46, and antenna 48. Ring electrode 42 and tip electrode 44 provide bipolar sensing of the electrogram (EGM) signal representing electrical activity of heart H. Fixation screw 46 holds sensor 16 in contact with the epicardium or other tissue near heart H. Sensor 16 processes the EGM signal sensed by electrodes 42 and 44, amplifies the EGM signal, and transmits the amplified signal through electrode 50 at the distal end of antenna 48 to SubQ ICD 12 and lead 14.

Signal processing circuitry within sensor 16 may analyze the EGM signal and either continuously transmit the EGM signal or transmit only if certain conditions, such as high or low heart rate conditions, are fulfilled or detected. The signal transmission between cardiac rhythm sensor 16 and SubQ ICD 12 may occur electrically through a large dipole electric field, via a radio frequency transmission by acoustic (e.g. ultrasonic) transmission, or by optical transmission. Either analog or digital transmission protocols can be used to transmit the cardiac rhythm signal from sensor 16 to SubQ ICD 12. Although antenna 48 is shown in FIG. 3 as extending from sensor 16, in other embodiments the antenna may be located on or within housing 40 of sensor 16.

Figure 4:
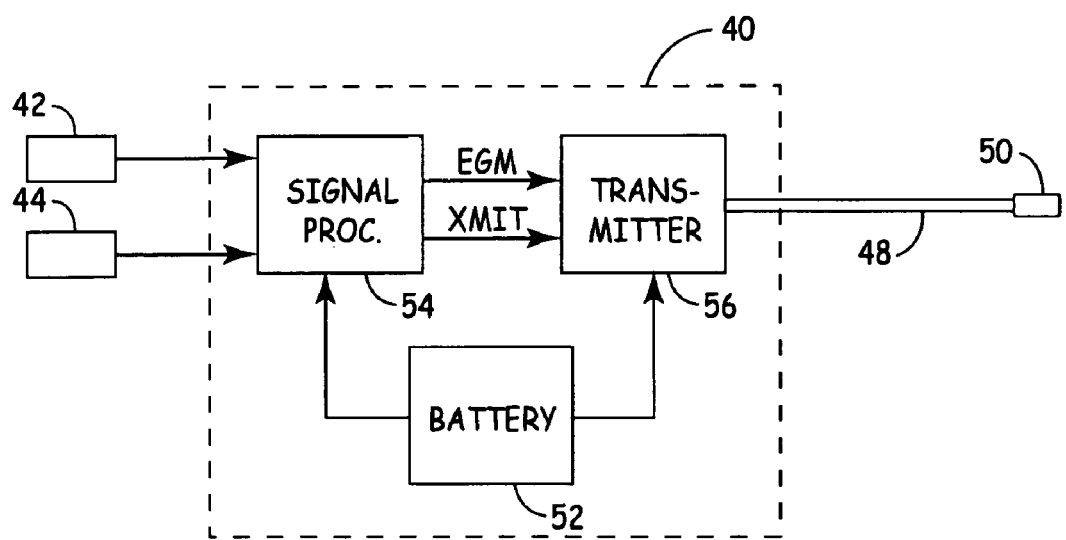
FIG. 4 is an electrical block diagram of the cardiac rhythm sensor.

FIG. 4 shows an electrical block diagram of cardiac rhythm sensor 16. Located within housing 40 are battery 52, signal processing circuitry 54, and transmitter 56. Battery 52 supplies the electrical energy required by signal processing circuitry 54 and transmitter 56. Signal processing circuitry 54 receives the EGM signal from ring electrode 42 and tip electrode 44. The EGM signal is filtered and amplified, and may also be analyzed by signal processing circuitry 54 to determine heart rate. Either analog or digital signal processing techniques may be used. Heart rate analysis of the EGM signal by signal processing circuitry 54 allows sensor 16 to transmit the cardiac rhythm signal only under conditions where therapy may be needed, rather than continuously. In the embodiment shown in FIG. 4, signal processing circuitry 54 provides the cardiac rhythm (EGM) signal and a transmit enable (XMIT) signal to transmitter 56 only when therapy may be needed.

In this embodiment, sensor 16 is sized to be implanted with a minimally invasive technique, such as with a trocar. The size of sensor 16 may be, for example, in the range of about 3 to about 10 mm in length and about 5 to about 10 mm in width or diameter. The small size of sensor 16 limits the battery size. Transmission of the cardiac rhythm signal only when a bradycardia or tachycardia condition exists, rather than continuous transmission of the signal, reduces the energy required by transmitter 56, and increases the battery life.

Figure 5:
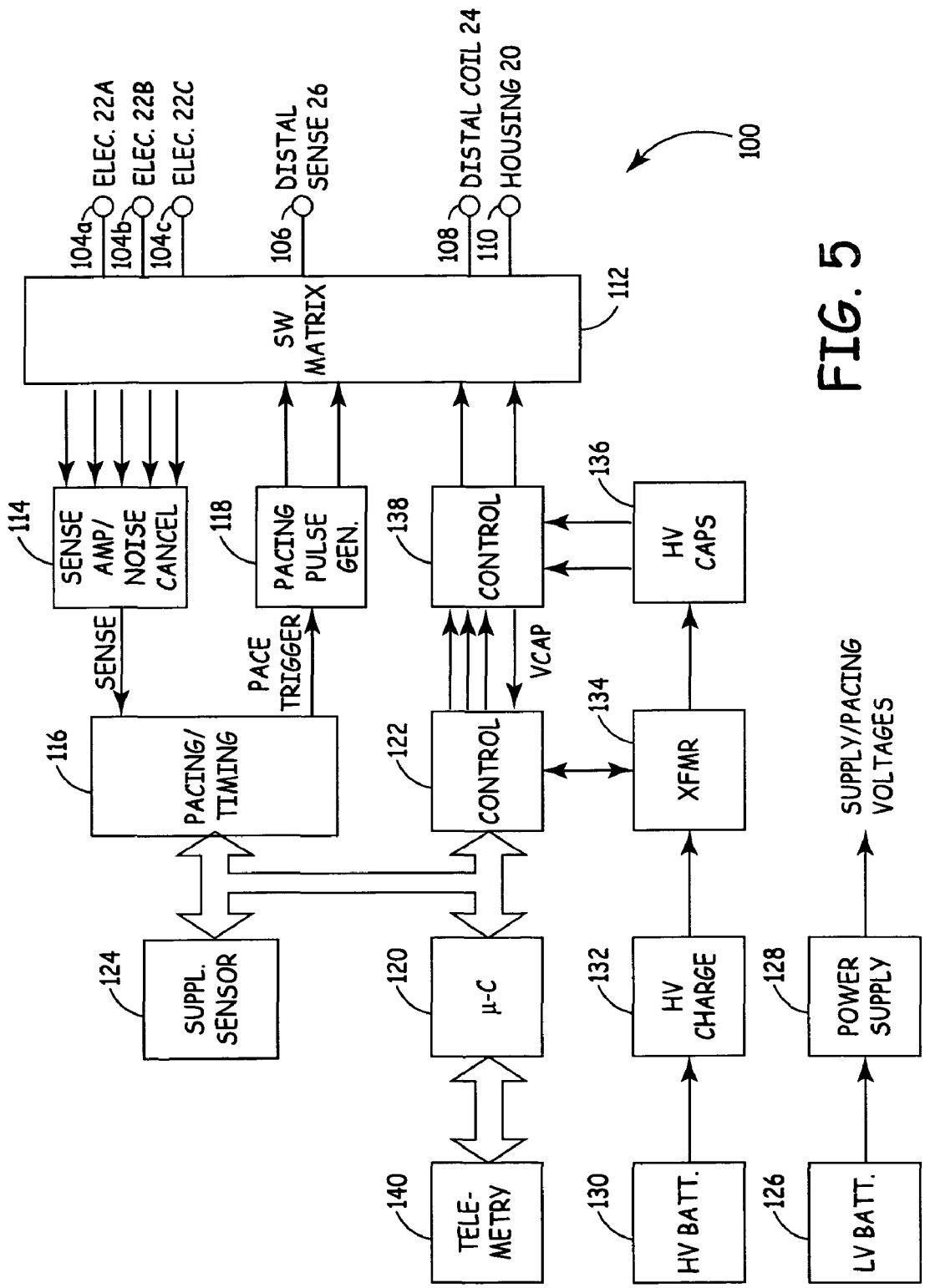
FIG. 5 is an electrical block diagram of the SubQ ICD.

FIG. 5 is a block diagram of electronic circuitry 100 of SubQ ICD 12. Circuitry 100, which is located within housing 20, includes terminals 104A-104C, 106, 108 and 110; switch matrix 112; sense amplifier/noise cancellation circuitry 114; pacing/timing circuit 116; pacing pulse generator 118; microcomputer 120; control 122; supplemental sensor 124; low-voltage battery 126; power supply 128; high-voltage battery 130; high-voltage charging circuit 132; transformer 134; high-voltage capacitors 136; high-voltage output circuit 138; and telemetry circuit 140.

Electrodes 22A-22C are connected to terminals 104A-104C. Electrodes 22A-22C act as sensing electrodes (along with distal sense electrode 26) to supply the cardiac rhythm signals received from sensor 16 through switch matrix 112 to sense amplifier/noise cancellation circuit 114. Electrodes 22A-22C also act as pacing electrodes to deliver pacing pulses from pacing pulse generator 118 through switch matrix 112.

Terminal 106 is connected to distal sense electrode 26 of subcutaneous lead 14. The cardiac rhythm signal from sensor 16, as sensed by distal sense electrode 26 is routed from terminal 106 through switch matrix 112 to sense amplifier/noise cancellation circuit 114.

Terminals 108 and 110 are used to supply a high-voltage cardioversion or defibrillation shock from high-voltage output circuit 138. Terminal 108 is connected to distal coil electrode 24 of subcutaneous lead 18. Terminal 110 is connected to housing 20, which acts as a common or can electrode for cardioversion/defibrillation.

Sense amplifier/noise cancellation circuit 114 and pacer/device timing circuit 116 process the cardiac rhythm signal as sensed by electrodes 22A-22C and 26. The cardiac rhythm signal is amplified and bandpass filtered by preamplifiers, sampled and digitized by analog-to-digital converters, and stored in temporary buffers.

Bradycardia is determined by pacer/device timing circuit 116 based upon R waves sensed by sense amplifier/noise cancellation circuit 114. An escape interval timer within pacer/device timing circuit 116 or control 122 establishes an escape interval. Pace trigger signals are applied by pacer/device timing circuit 116 to pacing pulse generator 118 when the interval between successive R waves sensed is greater than the escape interval.

Detection of malignant tachyarrhythmia is determined in control circuit 122 as a function of the intervals between R wave sense event signals from pacer/device timing circuit 116. This detection also makes use of signals from supplemental sensor(s) 124 as well as additional signal processing based upon the cardiac rhythm input signals.

Supplemental sensor(s) 124 may sense tissue color, tissue oxygenation, respiration, patient activity, or other parameters that can contribute to a decision to apply or withhold defibrillation therapy. Supplemental sensor(s) 124 can be located within housing 20, or may be located externally and carried by a lead to switch matrix 112.

Microcomputer 120 includes a microprocessor, RAM and ROM storage and associated control and timing circuitry. Detection criteria used for tachycardia detection may be downloaded from external programmer 18 through telemetry interface 140 and stored by microcomputer 120.

Low-voltage battery 126 and power supply 128 supply power to circuitry 100. In addition, power supply 128 charges the pacing output capacitors within pacing pulse generator 118. Low-voltage battery 126 can comprise one or two $LiCF_x$, $LiMnO_2$ or $LiI_2$ cells.

High-voltage required for cardioversion and defibrillation shocks is provided by high-voltage battery 130, high-voltage charging circuit 132, transformer 134, and high-voltage capacitors 136. High-voltage battery 130 can comprise one or two conventional $LiSVO$ or $LiMnO_2$ cells.

When a malignant tachycardia is detected, high-voltage capacitors 136 are charged to a preprogrammed voltage level by charging circuit 132 based upon control signals from control circuit 122. Feedback signal Vcap from output circuit 138 allows control circuit 122 to determine when high-voltage capacitors 136 are charged. If the tachycardia persists, control signals from control 122 to high-voltage output signal 138 cause high-voltage capacitors 136 to be discharged through the body and heart H between distal coil electrode 26 and the can electrode formed by housing 12.

Telemetry interface circuit 140 allows SubQ ICD 10 to be programmed by external programmer 18 through a two-way telemetry link. Uplink telemetry allows device status and other diagnostic/event data to be sent to external programmer 18 and reviewed by the patient's physician. Downlink telemetry allows external programmer 18, under physician control, to program device functions and set detection and therapy parameters for a specific patient.

In another embodiment, cardiac rhythm sensor 16 includes an accelerometer for sensing mechanical movement of heart H. Sensor 16 is attached by fixation screw 16, but does not require ring electrode 42 and tip electrode 44.

Although the present invention has been described with reference to preferred embodiments, workers skilled in the art will recognize that changes may be made in form and detail without departing from the spirit and scope of the invention.

What is claimed is:

1. An implantable cardioverter defibrillator (ICD) system comprising:
   a cardiac rhythm sensor for sensing cardiac activity and transmitting wirelessly a cardiac rhythm signal, wherein the cardiac rhythm sensor is configured to produce the cardiac rhythm signal only when a bradycardia or tachycardia condition exists;
   a subcutaneous implantable lead carrying a defibrillation electrode; and
   a subcutaneous implantable cardioverter defibrillator (SubQ ICD) for receiving the cardiac rhythm signal transmitted by the cardiac rhythm sensor and detecting tachycardia or bradycardia based on the cardiac rhythm signal, wherein the SubQ ICD is connected to the lead for providing electrical pulses to the defibrillation electrode upon the SubQ ICD detection of tachycardia or bradycardia based on the cardiac rhythm signal transmitted by the cardiac rhythm sensor to the SubQ ICD,
   wherein the SubQ ICD includes at least one electrode located on a housing of the SubQ ICD and configured to receive the cardiac rhythm signal and apply pacing pulses.

2. The ICD system of claim 1, wherein the cardiac rhythm sensor comprises:
   a plurality of electrodes for sensing an electrogram signal; and
   signal processing circuitry for filtering, analyzing and amplifying the electrogram signal.

3. The ICD system of claim 2, wherein the cardiac rhythm sensor further comprises:
   a transmitter for transmitting the electrogram signal.

4. The ICD system of claim 3, wherein the cardiac rhythm sensor further comprises:
   an antenna connected to the transmitter.

5. The ICD system of claim 3, wherein the signal processing circuitry produces the cardiac rhythm signal only when a bradycardia or tachycardia condition exists.

6. The ICD system of claim 3, wherein the signal processing circuitry selectively enables the transmitter based on analysis of the electrogram signal.

7. The ICD system of claim 1, wherein the cardiac rhythm sensor includes a motion sensing device for sensing mechanical activity of a heart.

8. The ICD system of claim 1, wherein the cardiac rhythm sensor is untethered to the SubQ ICD.

9. The ICD system of claim 1, wherein the cardiac rhythm sensor is sized to be implanted with a minimally invasive procedure.

10. The ICD system of claim 1, wherein the cardiac rhythm sensor has a length of less than about 10 mm and a width of less than about 10 mm.

11. The ICD system of claim 1, wherein the cardiac rhythm sensor includes an attachment device for attaching the cardiac rhythm sensor to cardiac tissue.

12. The ICD system of claim 1, wherein the at least one electrode of the SubQ ICD includes a sensing electrode.

13. The ICD system of claim 12, wherein the at least one electrode of the SubQ ICD includes a pacing electrode.

14. The ICD system of claim 1, wherein the lead carries a sensing electrode.

15. The ICD system of claim 1, wherein the cardiac rhythm sensor includes an accelerometer for sensing mechanical movement.

16. The ICD system of claim 1, further comprising an external programmer for programming the SubQ ICD.

17. An implantable cardioverter defibrillator (ICD) system comprising:
   a subcutaneous implantable lead;
   a subcutaneous implantable cardioverter defibrillator (SubQ ICD) including electrodes on a housing of the SubQ ICD for sensing and pacing;
   a cardiac rhythm sensor for sensing cardiac activity and transmitting wirelessly a cardiac rhythm signal to the SubQ ICD, wherein the cardiac rhythm sensor comprises a plurality of electrodes for sensing an electrogram signal, signal processing circuitry for filtering, analyzing and amplifying the electrogram signal, and a transmitter for transmitting a cardiac rhythm signal corresponding to the electrogram signal, wherein the cardiac rhythm sensor is configured to produce the cardiac rhythm signal only when a bradycardia or tachycardia condition exists.

18. The system of claim 17, wherein the subcutaneous implantable lead includes a defibrillation electrode and a sensing electrode.

19. The ICD system of claim 17, wherein the SubQ ICD includes an ovoid housing with a substantially kidney-shaped profile.

20. An implantable cardioverter defibrillator (ICD) system comprising:
   a subcutaneous implantable lead including a defibrillation coil electrode and a sensing electrode;
   a cardiac rhythm sensor including a ring electrode and a tip electrode for sensing cardiac activity and a distal electrode on an antenna for transmitting wirelessly a cardiac rhythm signal to the SubQ ICD, wherein the signal is only produced when a bradycardia or tachycardia condition exists; and
   a subcutaneous implantable cardioverter defibrillator (SubQ ICD) including canister electrodes positioned orthogonally to form signal vectors for receiving the cardiac rhythm signal transmitted by the cardiac rhythm sensor and detecting tachycardia or bradycardia based on the cardiac rhythm signal, wherein the SubQ ICD provides pacing pulses to the canister electrodes and is connected to the lead for providing electrical pulses to the defibrillation electrode upon the SubQ ICD detection of tachycardia or bradycardia based on the cardiac rhythm signal transmitted by the cardiac rhythm sensor to the SubQ ICD.

* * * * *